United States Patent [19]

Nelson et al.

[11] Patent Number: 4,829,092

[45] Date of Patent: May 9, 1989

[54] GLYCEROL AND DIGLYCEROL MIXTURES FOR SKIN MOISTURIZING

[75] Inventors: Bruce J. Nelson, Beacon Falls; Joseph D. Melnik, Stratford; William H. Schmitt, Branford, all of Conn.

[73] Assignee: Chesebrough-Pond's Inc., Greenwich, Conn.

[21] Appl. No.: 78,425

[22] Filed: Jul. 27, 1987

[51] Int. Cl.$^4$ ............................................. A61K 31/045
[52] U.S. Cl. ..................................... 514/738; 514/844; 514/846; 514/847; 514/873
[58] Field of Search ............... 514/738, 844, 846, 847, 514/873

[56] References Cited

U.S. PATENT DOCUMENTS

| 4,250,193 | 2/1981 | Ochiai et al. | 424/358 |
| 4,263,284 | 4/1981 | Schreuder | 424/180 |
| 4,370,319 | 1/1983 | Chapin et al. | 424/184 |
| 4,421,769 | 12/1983 | Dixon et al. | 514/847 |
| 4,504,464 | 3/1985 | Takaishi et al. | 424/63 |

FOREIGN PATENT DOCUMENTS 0183608  10/1983  Japan ................................. 514/844

OTHER PUBLICATIONS

Sugiyama et al. (I) CA 80 #124594t (1974).
Sugiyama et al. (II) CA 81 #96335j (1974).
Daicel CA 101 #72269w (1984).
Ochiai et al. (II) Official Gazette p. 1071 1/87.
Shiseido (II) CA 100 #108980s (1984).
Yamada et al. CA 104 #10394m (1986).

*Primary Examiner*—Leonard Schenkman
*Attorney, Agent, or Firm*—Melvin H. Kurtz

[57] ABSTRACT

A synergistic moisturizing effect can be obtained in skin treating, e.g., cosmetic, formulations utilizing a combination of glycerol and diglycerol.

4 Claims, 4 Drawing Sheets

GLYCEROL AND DIGLYCEROL MIXTURES FOR SKIN MOISTURIZING

BACKGROUND OF THE INVENTION

The present invention relates to novel skin conditioning compositions which are retentive on skin thereby reducing moisture loss from the skin surface.

Various agents have been used in the treatment of human skin to keep the skin in a smooth and supple condition. Skin has the tendency to dry out when exposed to conditions of low humidity or to extended periods in a detergent solution. From a biochemical standpoint, dryness is a measure of the water content of the skin. Inasmuch as the water content and vapor pressure of the epidermis under normal conditions are higher than those of the surrounding air, water evaporates from the skin surface. The skin becomes dry because of loss of moisture from the surface and the subsequent loss of water from the stratum corneum.

Continuous or prolonged immersion in soap or detergent can contribute to dryness of the stratum corneum in that the surfactant medium promotes dissolution of the stratum corneum lipids or epidermal lipids, and the hydroscoic water-soluble components in the corneum.

To alleviate skin dryness, emollient creams have been recommended for application to the skin. The active ingredients in emollient creams probably increase the state of hydration of the corneous layer of the skin by altering the rate of diffusion of water from the skin layers, the rate of evaporation of water from the stratum corneum lipids or epidermal lipids and the ability of the corneous layer to hold moisture.

A wide variety of materials have been disclosed for alleviating the problems of dry skin. A number of polyalcohols or derivatives such as glycerol and glycerol ethers have been used. Glycerol is frequently used because of its excellent humectant properties. Glycerol ethers such as the monoalkyl ethers have found wide spread commercial utility as base materials for cosmetic compositions.

It has been reported that diglycerol can be used as a moistening agent in cosmetic preparations (Japanese Kokai No. 74 41 545-Chem. Abstr., 81 1974 96335j and Japanese Kokai No. 73 91 231-Chem. Abstr., 80 1974 124594t). An emollient cream is disclosed containing beeswax, stearic acid, polawax, various oils, isopropyl myristate, preservatives, and perfumes.

BRIEF SUMMARY OF THE INVENTION

It has now been found that a synergistic moisturizing effect can be obtained utilized a combination of glycerol and diglycerol. A higher moisture retention value is obtained for the combination over and above that amount that would be expected from each component itself. This combination can be used in various cosmetic creams, lotions, liquids, powders and pastes.

The synergistic effect of the blend is unexpected since the polyethers of glycerol are, in general, less effective humectants than glycerol itself, particularly as the number of repeating glycerol groups in the polyether increases.

DETAILED DESCRIPTION OF THE INVENTION

Figure 1:
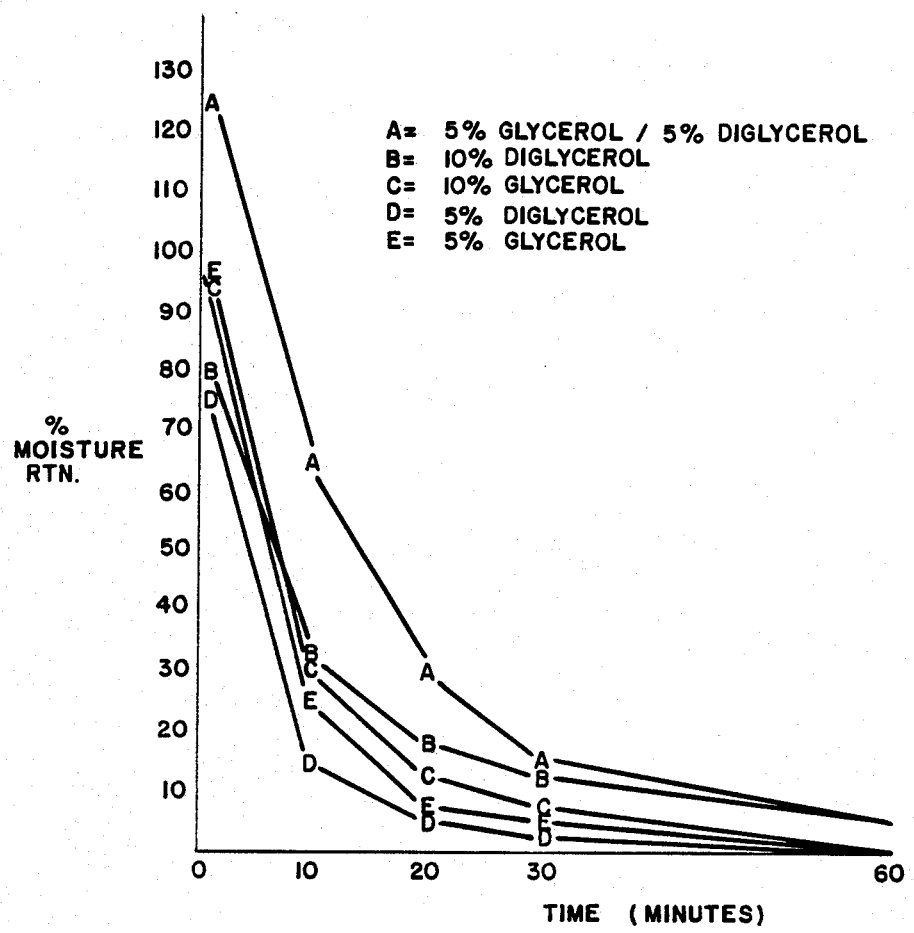
FIG. 1 is a graph showing the effectiveness of the composition of the invention based on the data of Example 1.

Diglycerol is generally considered a diether of glycerol. The material is generally a clear, odorless, colorless viscous liquid having a boiling point of approximately 205° C. at 1 mm Hg pressure. The produce has a molecular weight of approximately 166, has four pendant hydroxy groups, and has a viscosity of about 280 centistokes at 65° C.

The diglycerol can be used in a weight ratio to glycerol ranging from 90:10 to about 10:90, preferably from about 75:25 to about 25:75 with preferred results being obtained at weight ratios of from about 40:60 to about 60:40. This combination can be used in an amount sufficient to provide a humectant effect in a final use product. The synergistic admixture can be used as a direct replacement for humectants in present formulations in like amounts. Preferably, the combination is used in an amount ranging from about 1% to about 30%, based on the total weight of the ingredients (including water) in the final composition.

The humectants of the present invention can be used in any composition which presently uses humectants, primarily cosmetics, though the compositions of the invention can be used in other areas, such as pharmaceutical creams and lotions for topical application and in food products. In the preferred cosmetics area, the compositions of the invention can be used in such products as antiperspirants; bath and shower soaps, granules, bars, oils or gels; after-bath creams and lotions; shampoo and conditioners; makeup including base or foundation, blush, rouge, eye liner, eye shadow, mascara, and lip gloss; lip moisturizers and lip ointment; message creams and lotions; sun screen, sun tanning and skin bleaching compositions; skin paint; wrinkle remover; cold creams, cleansing creams, emollient creams and hand creams; perfume and fragrances; hair waving, bleaching, setting products, rinses and dressings; insect repellents, preshave and after-shave lotions and creams, shave creams, depilatories and the like. The products can be in the form of creams, lotions, liquids, powders, pastes, and the like, as would be appreciated by one of ordinary skill in the art.

In addition to the glycerol/diglycerol combination, the final product, such as a cosmetic lotion or cream, can contain any of those various ingredients normally included within compositions of those types.

In general, most cosmetic and pharmaceutical creams and lotions contain oils, waxes, lanolins, sterols, humectants, emollients, thickening agents, proteins, preservatives, emulsifiers, silicones and the like as would be appreciated by one of ordinary skill in the art. These materials and specific formulations are more fully illustrated in "Cosmetics; Science & Technology", Second Ed., Vol. 1, Ed. Board—M. S. Balsam et al., Wiley Interscience, 1972, particularly pages 27–105 and 179–222; and "Cosmetic and Toiletry Formulations:, E. W. Flick, Noyes Publications, 1984, The disclosures of which are incorporated herein by reference. The amounts of these components utilized have been outlined in the above references and would also be well appeciated by one of ordinary skill in the art.

The present compositions may also contain agents suitable for aesthetic purposes such as perfumes and dyes. These agents may be used in amounts sufficient to achieve the desired fragrance and color.

The pH of the present compositions is preferably in the range of about 4.5–9.0.

The final use compositions of the present invention generally have a cream or lotion consistency and may be in the form of oil-in-water or water-in-oil emulsions with the former being preferred because of their more pleasing cosmetic properties. Methods of manufacturing the products are well known ("*Cosmetics; Science & Technology*", Ibid) and can be used in preparing compositions including the humectant composition of the present invention.

The compositions of the present invention are useful in the skin care field generally. They are used in an amount sufficient to meet the individual user's needs and desires.

The present invention is more fully illustrated in the Examples which follow.

EXAMPLE 1

The combination of glycerol and diglycerol as an efficacious moisturizer was examined used an in vitro porcine skin assay. 4×1 centimeter pieces of hairless porcine skin were rinsed to remove irradiation residue, dried for more than 48 hours at 0% relative humidity and weighed. Pieces of skin were hydrated for 5 minutes in aqueous test solutions containing 10% (V/V) of the material being tested. The skin samples were then patted dry.

The skin samples were dehydrated for 24 hours in a desiccator at 0% relative humidity and weighed (Product Residue-%).

The samples were rehydrated for 24 hours at 100% relative humidity. The samples were allowed to dry while on an electric balance in an atmosphere of less than 10% relative humidity. Sample weights were taken at 0 minutes (moisture pickup-%) and after 10, 20, 30 and 60 minutes (Moisture Retention 10, 20, 30 and 60-%). The samples were then rinsed for 5 minutes in deionized water, dried for 24 hours and weighed to determine skin adherence or substantivity under wash conditions (Substantivity-%).

The percent residue values were calculated as follows:

Residue weight—dry skin weight/dry skin weight × 100

The percent moisture values were calculated as follows:

Weight of moisturized skin—residue weight/residue weight × 100

The percent substantivity values were calculated as follows:

$$\frac{\text{Substantivity weight} - \text{dry weight}}{\text{dry weight}} \times 100$$

These values were averaged for the number of pieces of treated skin.

The following results were obtained. The data for moisture retention is further visually represented in FIG. 1.

TABLE I

| Sample | A | B | C | D* | E* |
|---|---|---|---|---|---|
| Glycerol | 5 | | 10 | | 5 |
| Diglycerol | 5 | 10 | | 5 | |
| Residue-% | 10.26 | 7.45 | 11.21 | 6.44 | 6.52 |
| Moisture Pickup-% | 125.71 | 82.41 | 96.64 | 74.22 | 99.84 |
| Moisture Retention-% | | | | | |
| 10 minutes | 65.81 | 33.59 | 30.83 | 15.86 | 25.04 |
| 20 minutes | 28.63 | 16.84 | 11.21 | 5.30 | 6.80 |
| 30 minutes | 14.30 | 12.22 | 5.62 | 2.96 | 3.74 |
| 60 minutes | 6.15 | 7.92 | .91 | 0.47 | 1.14 |
| Substantivity-% | −1.66 | 1.80 | 3.28 | 4.22 | 3.19 |

*5% solution of active material instead of 10%. Results are mean of 6 samples except for Example 3 which is the mean for 18 samples for moisture data and 12 samples for substantivity.

As it can be seen from the data, the combination of 5% glycerol/5% diglycerol provides an increased moisture pickup and moisture retention greater than that provided by 10% of either agent alone, and significantly greater than those results expected from the additive total of the two at the same concentration level (5%). The moisture retention provided by the 5%:5% blend of glycerol/diglycerol after 60 minutes is substantially equivalent to that provided by diglycerol at the 10% level, 6.15% vs. 7.92%. The moisture retention after 60 minutes for glycerol has been reduced to less than 1. At 5% diglycerol, the moisture retention after 60 minutes is 1/14 that of the blend and at 5% glycerol the moisture retention after 60 minutes is 1/6 that of the blend. This data shows that an effect beyond an additive effect of the two compositions has been obtained.

EXAMPLE 2

A commercial hand care lotion was formulated using a blend of 2.5 parts glycerol/2.5 parts diglycerol in place of the 5 parts glycerol normally used in the lotions, the following formulation was used:

| | Parts |
|---|---|
| Water | 80.66 |
| Glycerin | 2.5 |
| Diglycerol | 2.5 |
| Mineral Oil (70 viscosity) | 3.0 |
| Acylic polymer crosslinked with allyl sucrose (Goodrich) (Carbopol Dispersion - 2%) | 3.0 |
| Stearic Acid | 2.5 |
| Glycol Stearate Opacifier | 1.5 |
| Acetylated Lanolin Alcohol | 1.0 |
| Triethanolamine | 1.0 |
| Glycerol Monostearate | 0.7 |
| Cetyl Alcohol | 0.3 |
| Dimethicone | 0.2 |
| Magnesium Aluminum Silicate | 0.2 |

The lotion also contained methyl and propyl paraben as well as disodium EDTA as preservatives, color and fragrance.

The product was tested as in Example 1 with the following results:

| Sample | F | G Commercial Product | H Untreated Control |
|---|---|---|---|
| Glycerol | 2.5% | 5% | |
| Diglycerol | 2.5% | | |
| Residue-% | 13.21 | 4.42 | −1.92 |
| Moisture Pickup | 88.42 | 86.20 | 61.4 |
| Moisture Retention | | | |
| 10 | 50.71 | 56.5 | 22.77 |
| 20 | 33.49 | 34.16 | 12.93 |
| 30 | 24.99 | 20.27 | 10.04 |
| 60 | 14.58 | 7.92 | 4.08 |

-continued

| Sample | F | G Commercial Product | H Untreated Control |
|---|---|---|---|
| Substantivity-% | 0.51 | 3.60 | −1.11 |

The product of Sample F showed a significantly greater percent residue over that of the commercial lotion (G). Maximum moisture uptake was substantially equivalent between the product of the invention (F) and the commercial product (G). At moisture retentions of 10 and 20 minutes, the dry out between the two samples was essentially the same. At 30 minutes the moisture retention curves begin to deviate. After 60 minutes the products are significantly different.

The percent substantivity of the commercial product is significantly greater than the product of the invention. For overall performance, the total areas under the curve representing total moisturization and moisture retention (Sample F=2003, Sample G=1862) exhibits a trendwise but not a significant different in performance between the two though the performance is balanced in favor of the product of the invention due to the enhanced moisture retention after 60 minutes of dry out.

We claim:

1. A humectant for skin treating composition comprising, a synergistic combination, of glycerol and diglycerol in a ratio by weight of about 1:1.

2. A hand lotion or cream comprising, as humectant therefore, the composition of claim 1.

3. A skin treating composition including as humectant therefore the product of claim 1.

4. The composition as recited in claim 3 which further includes a member selected from the group consisting of emulsifiers, silicone fluids, emollients, additional humectants, thickening agents, preservatives, colorings, fragrances and mixtures thereof, said members being adapted for treatment of skin.

* * * * *